(12) United States Patent
Cruse

(10) Patent No.: US 7,169,872 B2
(45) Date of Patent: Jan. 30, 2007

(54) HYBRID SILICON-CONTAINING COUPLING AGENTS FOR FILLED ELASTOMER COMPOSITIONS

(75) Inventor: Richard W. Cruse, Yorktown Heights, NY (US)

(73) Assignee: General Electric Co., Schenectady, NY (US)

( * ) Notice: Subject to any disclaimer, the term of this patent is extended or adjusted under 35 U.S.C. 154(b) by 0 days.

(21) Appl. No.: 10/137,463

(22) Filed: Apr. 30, 2002

(65) Prior Publication Data
US 2003/0055139 A1    Mar. 20, 2003

Related U.S. Application Data

(60) Provisional application No. 60/287,888, filed on Apr. 30, 2001.

(51) Int. Cl.
*C08G 77/08*    (2006.01)
(52) U.S. Cl. .............................. 528/14; 528/30; 528/23; 556/427
(58) Field of Classification Search ................. 528/30, 528/14, 23; 525/100; 556/427
See application file for complete search history.

(56) References Cited

U.S. PATENT DOCUMENTS

| | | | | |
|---|---|---|---|---|
| 4,044,037 A | * | 8/1977 | Mui et al. ...................... | 528/30 |
| 4,595,740 A | * | 6/1986 | Panster ......................... | 528/30 |
| 5,674,932 A | * | 10/1997 | Agostini et al. ............. | 524/430 |
| 5,998,548 A | | 12/1999 | Brennenstuhl et al. | |
| 6,001,948 A | | 12/1999 | Scheim et al. | |
| 6,013,718 A | | 1/2000 | Cabioch et al. | |
| 6,018,011 A | | 1/2000 | Scheim et al. | |
| 6,020,068 A | | 2/2000 | Kawazura et al. | |
| 6,020,449 A | | 2/2000 | Scheim | |
| 6,331,605 B1 | * | 12/2001 | Lunginsland et al. ......... | 528/30 |

FOREIGN PATENT DOCUMENTS

| | | |
|---|---|---|
| AU | A10082974 | 7/1997 |
| DE | 19957325 A1 | 5/2001 |
| EP | 784072 | 7/1997 |
| EP | 1002835 A2 | 5/2000 |
| WO | WO 9909036 | 2/1999 |

OTHER PUBLICATIONS

Veronkov et al, "The Siloxane Bond—Physical Properties and Chemical Transformation" Inst. Of Organic Chem. Academy of Sciences of the USSR. Moscow (1961).

* cited by examiner

*Primary Examiner*—Margaret G. Moore

(57) ABSTRACT

This invention describes novel chemical compounds whose structures are hybrids between sulfur-containing and non-sulfur-containing silanes wherein the two types of silanes are linked by siloxane bonds. The invention includes methods of preparation for the hybrid silanes as well as their use in filled rubbers as coupling agents. The hybrid silanes described are unique in that a certain amount of water in their preparation leads to superior performance in their intended application, and that they can thus be produced more efficiently and safely than coupling agents currently used in the art, from readily available hydrated raw materials.

6 Claims, No Drawings

HYBRID SILICON-CONTAINING COUPLING AGENTS FOR FILLED ELASTOMER COMPOSITIONS

CROSS-REFERENCE TO RELATED APPLICATION

This application claims priority to U.S. Provisional Application No. 60/287,888, filed Apr. 30, 2001.

FIELD OF THE INVENTION

This invention relates to silane coupling agents for use in filled elastomer compositions, and in particular, rubber compounding. The coupling agents of the present invention are distinguished in that their molecular structure is a hybrid of two structural entities, each containing a unique type of silicon ultimately uniting polymer and filler in the final composition.

BACKGROUND OF THE INVENTION

The vast majority of prior art in the use of coupling agents in rubber involves silane molecules containing one or two, and in less frequent cases, up to several silicon atoms bound to any one of a wide number of sulfur-functional groups. Each silicon is almost exclusively bound to one or more simple hydrolyzable alkoxy group in the practiced art. Sulfur is indirectly bonded to the silicon chemically via a backbone of one to several carbon atoms. These sulfur silane coupling agents function by chemically bonding silica to polymer used in rubber applications in a relatively simple and straight forward manner. Coupling is accomplished by chemical bond formation between the silane sulfur and the polymer and by hydrolysis of the silane alkoxy groups and subsequent condensation with silica hydroxyl groups.

Commonly used coupling agents typically contain silicon exclusively bound to carbon and alkoxy groups, and need to be manufactured using anhydrous alcoholic solutions of sulfur anions of alkali metal ions or the ammonium ion. Anhydrous materials must be used so as to preserve the hydrolytically labile alkoxy groups present on silicon. Despite the low cost and general availability of hydrated sodium sulfide, polysulfide, and hydrosulfide salts, anhydrous analogs are not easily obtained or handled because of their great affinity for water. The removal of water from hydrous materials requires conditions conducive to fire hazards and usually does not go to completion. Preparations of anhydrous materials by indirect methods are costly and involve raw materials, such as metallic sodium and hydrogen sulfide, which pose special hazards during use and transportation. Thus, it would be beneficial from a safety and economic standpoint to use starting materials which do not require anhydrous conditions or reagents.

The use of mixtures of separate silicones and sulfur silanes in tire applications is known in the art and for instance, is described in European Patent EP 0 784 072 A1 wherein individual silicon containing chemical compounds are blended, either prior to incorporation into the rubber compound, or by being sequentially added to the rubber compound. Thus, it would be advantageous to have a single compound which provides the benefits obtainable from the separate silicones and sulfur silanes thereby eliminating additions during the rubber compounding.

Bearing in mind the problems and deficiencies of the prior art, it is therefore an object of the present invention to provide a sulfur silane which can be made under non-anhydrous conditions.

It is another object of the present invention to provide a sulfur silane having the advantages of a both a sulfur containing silane and a silicone.

SUMMARY OF THE INVENTION

The silicon-containing chemical compounds of the present invention, hereinafter referred to as "hybrid silane compositions", are novel hybrid sulfur silane coupling agents. They are comprised of distributions of novel molecules, herein referred to as "hybrid silanes", which are siloxane hybrid molecules of two distinct types of alkoxy silanes. The hybrid silanes are hybrids in the sense that one or more pairs of alkoxy groups, one each from a silicon atom of each of the two alkoxy silane types, have been replaced by an equal number (i.e., number of oxygen atoms equals the number of pairs of alkoxy groups) of oxygen atoms, which bridge the originally separate structures into a single molecule, via an equal number (i.e., number of new Si—O—Si linkages equals the number of pairs of alkoxy groups) of new Si—O—Si linkages. The two aforementioned distinct types of alkoxy silanes are sulfur-containing alkoxysilanes, herein referred to as "sulfur silanes", and hydrocarbon-functionalized alkoxysilanes, herein referred to as "alkylalkoxysilanes".

The hybrid silane compositions optionally also contain the individual sulfur silanes and alkylalkoxysilanes, themselves; partial or full condensation products of the individual sulfur silanes; and partial or full condensation products of the individual alkylalkoxysilanes. The hybrid silanes exhibit advantages both in use and from a manufacturing standpoint over conventional sulfur-containing alkoxysilanes, such as TESPT and TESPD (the nominal triethoxysilylpropyl tetrasulfide and triethoxysilylpropyl disulfide, respectively), currently being used in the tire and rubber industry.

The present invention further relates to a novel process for manufacturing the hybrid silanes wherein the presence of water is not only tolerated, but moreover sought, leading to a safer process and lower cost product.

In addition, the present invention further relates to the use of the hybrid silanes in a rubber composition, particularly useful in tires, wherein the rubber composition comprises at least one crosslinkable rubber and a filler.

The crosslinkable rubber is preferably a conjugated diene homopolymer or copolymer, or a copolymer of at least one conjugated diene and aromatic vinyl compound. The filler is preferably at least one of siliceous fillers; carbon black; clays; inorganic oxides such as alumina and titania, and their silicates; and multiple phase fillers composed of individual phases of the aforementioned fillers, such as carbon-silica dual phase fillers. The filler is more preferably a mixture of such fillers such as carbon black or carbon black and at least one siliceous filler.

The use of these silanes in the manufacture of inorganic filled elastomers is taught wherein processing advantages and/or more desirable end products are realized, which can be achieved with neither the individual structural components of the hybrid silanes alone, nor with mere mixtures of these structural components.

DETAILED DESCRIPTIONS OF THE PREFERRED EMBODIMENT(S)

The hybrid silanes of the present invention are sulfur silane-silicone hybrids useful as coupling agents for elastomers and fillers. The hybrid silanes described in the present invention are composed of single components or mixtures of molecules whose individual chemical structures can be represented by the following general formula, $$F^1_r F^2_s \quad \text{Formula (I)}$$

wherein
r is 0 to 10,000;
s is 0 to 10,000;
$F^1$ has one of the general structures, $$\{(R^1O)_{3-m-n}[(-O-)_{0.5}]_m R^2_n Si\text{-}G^1\text{-}S_x\text{-}(C=E)_y\text{-}E_z\}_p\text{-}G^2 \quad \text{Formula (II)}$$

or $$\{(R^1O)_{3-m-n}[(-O-)_{0.5}]_m R^2_n Si\text{-}G^1\text{-}S_x\text{-}\}_2(C=E)_y \quad \text{Formula (III)}$$

wherein
each occurrence of $R^1$ and $R^2$ is independently hydrogen, or any group which can be obtained by removal of one hydrogen atom from a hydrocarbon group having from 1 to 20 carbon atoms, including branched or straight chain alkyl, alkenyl, aryl or aralkyl groups;
each occurrence of $G^1$ is any group which can be obtained by removal of a quantity of two hydrogen atoms from any hydrocarbon having from 1 to 20 carbon atoms;
each occurrence of $G^2$ is independently a hydrogen atom or any group which can be obtained by removal of a quantity of p hydrogen atoms from any hydrocarbon having from 1 to 20 carbon atoms;
S is sulfur;
O is oxygen;
Si is silicon;
each occurrence of E is independently oxygen or $S_x$;
each occurrence of m and n is independently 0, 1 or 2;
each occurrence of p is independently 1 to 4;
each occurrence of y and z is independently 0 or 1; and
each occurrence of x is independently 1 to 8;
$F^2$ is represented by the general structure:

$$(R^1O)_{4-m'-n'}[(-O-)_{0.5}]_{m'} R^3_{n'} Si \quad \text{Formula (IV)}$$

wherein
each occurrence of $R^1$ is as defined above:
each occurrence of $R^3$ is independently hydrogen, or a hydrocarbon group of 1 to 20 carbon atoms including aryl as well as branched or straight chain alkyl, alkenyl, arenyl, or aralkyl groups; and
each occurrence of m' and n' can be independently 0, 1, 2 or 3.

It is also possible that m' may be 4, but with the provisos that 1) the quantities of silicon atoms when m' is equal to 4 are not aggregated together in quantities in excess of that which would arise from the synthetic methods described below, 2) that the product is prepared by one of the methods described below, and 3) that silica is not used as a raw material in the manufacturing process, which would give rise to aggregates of silica in which m' is equal to 4.

The hybrid silane compositions of the present invention are further characterized in that they are comprised of at least one hybrid silane; that is, they are comprised of at least one chemical compound in which r and s of Formula (I) above each have a value of at least 1.

All $G^1$ and all $G^2$ containing at least one carbon atom are herein referred to as divalent hydrocarbon groups and p-valent hydrocarbon groups, respectively. Thus, as used herein, a divalent hydrocarbon group is understood to mean any hydrocarbon from which a quantity of two hydrogen atoms have been removed and a p-valent hydrocarbon group is understood to mean any hydrocarbon from which a quantity of p hydrogen atoms have been removed.

The $F^1$ and/or $F^2$ components of any of the structures given by Formula (I) are chemically linked by a quantity of Si—O—Si bonds given by (m and m')/2. In each of these Si—O—Si bonds, an oxygen atom is bonded to two silicon atoms. Each of these two silicon atoms occurs in one of each $F^1$ or each $F^2$. Each of the oxygen atoms in any of the structures given by Formula (I) constitutes a chemical link (Si—O—Si bond) between silicon atoms of $F^1$ and $F^2$; between silicon atoms of $F^1$ and another like or different $F^1$; between silicon atoms of $F^2$ and another like or different $F^2$; or between two silicon atoms within a single $F^1$. The hybrid silane compositions of the present invention comprise at least one hybrid silane whose structure according to Formula (I) contains at least one Si—O—Si bond between one silicon atom of a structure given by $F^1$ and one silicon atom of a structure given by $F^2$. In practice the hybrid silane compositions, although they need not, often will contain many hybrid silanes whose structures according to Formula (I) contain more than one Si—O—Si bond between silicon atoms of structures given by $F^1$ and silicon atoms of structures given by $F^2$, as well as silanes whose structures according to Formula (I) contain Si—O—Si bond(s) between silicon atoms within the same or from two like or different structures given by $F^1$ alone, as well as siloxanes whose structures according to Formula (I) contain an Si—O—Si bond between silicon atoms from two like or different structures given by $F^1$ alone. In addition, the hybrid silane compositions of the present invention may, but need not, contain components whose structures given by $F^1$ and $F^2$ contain no Si—O—Si bond; that is, structures wherein m and m', respectively, are zero. These structures would correspond to individual molecules of sulfur silane and alkylalkoxysilane, respectively.

The structures of $F^1$ are molecular fragments derived from sulfur-containing alkoxysilanes in which a quantity m of the alkoxy groups have been removed. Thus, when m is 0, the structure of $F^1$ would represent a sulfur-containing alkoxysilane. Any such m is 0 specie will hereinafter be referred to as a "sulfur silane". An analog species where m is greater than 0 will hereinafter be referred to as a "sulfur silane condensate".

The structures of $F^2$ are molecular fragments derived from hydrocarbon group-containing alkoxysilanes in which a quantity m of the alkoxy groups have been removed. Thus, when m is equal to 0, the structure of $F^2$ would represent a hydrocarbon group-containing alkoxysilane. Any such m is equal to 0 specie will hereinafter be referred to as an "alkylalkoxysilane". An analog species where m is equal to 0 will hereinafter be referred to as an "alkylalkoxysilane condensate". Any member of the group collectively consisting of the structures for $F^1$ and $F^2$ when m is equal to 0 will herein be referred to as an "alkoxysilane", and similarly, any member of the group collectively consisting of the structures for $F^1$ and $F^2$ when m is greater than 0 will herein be referred to as an "alkoxysilane condensate".

As used herein, alkyl includes straight, branched and cyclic alkyl groups; alkenyl includes any straight, branched, or cyclic alkenyl group containing one or more carbon-carbon double bonds, where the point of substitution can be either at a carbon-carbon double bond or elsewhere in the group; and alkynyl includes any straight, branched, or cyclic alkynyl group containing one or more carbon-carbon triple bonds and optionally also one or more carbon-carbon double bonds as well, where the point of substitution can be either at a carbon-carbon triple bond, a carbon-carbon double bond, or elsewhere in the group. Specific examples of alkyls include methyl, ethyl, propyl, isobutyl. Specific examples of alkenyls include vinyl, propenyl, allyl, methallyl, ethylidenyl norbornane, ethylidene norbornyl, ethylidenyl norbornene, and ethylidene norbornenyl. Specific examples of alkynyls include acetylenyl, propargyl, and methylacetylenyl. As used herein, aryl includes any aromatic hydrocarbon from which one hydrogen atom has been removed; aralkyl includes any of the aforementioned alkyl groups in which one or more hydrogen atoms have been substituted by the same number of like and/or different aryl (as defined herein) substituents; and arenyl includes any of the aforementioned aryl groups in which one or more hydrogen atoms have been substituted by the same number of like and/or different alkyl (as defined herein) substituents. Specific examples of aryls include phenyl and naphthalenyl. Specific examples of aralkyls include benzyl and phenethyl. Specific examples of arenyls include tolyl and xylyl. As used herein, cyclic alkyl, cyclic alkenyl, and cyclic alkynyl also include bicyclic, tricyclic, and higher cyclic structures, as well as the aforementioned cyclic structures further substituted with alkyl, alkenyl, and/or alkynyl groups. Representative examples include norbornyl, norbornenyl, ethylnorbornyl, ethylnorbornenyl, ethylcyclohexyl, ethylcyclohexenyl, cyclohexylcyclohexyl, and cyclododecatrienyl.

Representative examples of sulfur silanes of the present invention, $F^1$ (i.e., with m=0), include bis-(3-triethoxysilyl-1-propyl)thioether, bis-(3-triethoxysilyl-1-propyl)disulfide, bis-(3-triethoxysilyl-1-propyl)trisulfide, bis-(3-triethoxysilyl-1-propyl)tetrasulfide (TESPT), bis-(3-triethoxysilyl-1-propyl)pentasulfide, bis-(3-triethoxysilyl-1-propyl)hexasulfide, bis-(3-triethoxysilyl-1-propyl)heptasulfide, bis-(3-triethoxysilyl-1-propyl)octasulfide, or any mixtures thereof; bis-(triethoxysilylmethyl)disulfide, bis-(triethoxysilylmethyl)tetrasulfide; bis-(2-triethoxysilyl-1-ethyl)disulfide, bis-(2-triethoxysilyl-1-ethyl)tetrasulfide, bis-(1-triethoxysilyl-1-ethyl)disulfide, bis-(1-triethoxysilyl-1-ethyl)tetrasulfide, bis-(3-triethoxysilyl-1-propyl)dithiocarbonate, bis-(3-triethoxysilyl-1-propyl)trithiocarbonate, bis-(3-trimethoxysilyl-1-propyl)tetrasulfide, and bis-(3-triisopropoxysilyl-1-propyl)disulfide.

Representative examples of alkylalkoxysilanes of the present invention, $F^2$ (i.e., with m=0), include tetraethoxysilane, tetramethoxysilane, triethoxysilane, tetraisopropoxysilane, tetrapropoxysilane, methyltriethoxysilane, methyltrimethoxysilane, ethyltriethoxysilane, propyltriethoxysilane, propyltrimethoxysilane, phenyltriethoxysilane, phenyltrimethoxysilane, octyltriethoxysilane, octyltrimethoxysilane, octadecyltriethoxysilane, and octadecyltrimethoxysilane.

Representative examples of $R^1$ include methyl, ethyl, propyl, isopropyl, butyl, phenyl, and benzyl. Methyl, ethyl, and isopropyl are preferred. Ethyl is most preferred. Representative examples of $R^2$ include hydrogen, methyl, ethyl, propyl, isopropyl, sec-butyl, phenyl, vinyl, cyclohexyl, and higher straight-chain alkyl, such as butyl, hexyl, octyl, lauryl, and octadecyl. Methyl, ethyl, phenyl, and the higher straight-chain alkyl are preferred. Methyl and phenyl are most preferred. Representative examples of $R^3$ include hydrogen, methyl, ethyl, propyl, isopropyl, sec-butyl, phenyl, vinyl, cyclohexyl, and higher straight-chain alkyl, such as butyl, hexyl, octyl, lauryl, octadecyl, ethylcyclohexyl, ethylnorbornyl, ethylcyclohexenyl, ethylnorbornenyl, divinylcyclohexylethyl, and phenethyl. Methyl, ethyl, phenyl, and the higher straight-chain alkyl are preferred. Methyl, octyl, octadecyl, and phenyl are most preferred.

Representative examples of $G^1$ include —$CH_2$—, —$CH_2CH_2$—, —$CH_2(CH_2)_aCH_2$— in which the quantity, a, is an integer of from 1 to 16, -phenylene-, —$CH_2$-phenyl-, —$CH_2CH_2$-phenyl-, and —$CH(CH_3)$—. The structures, —$CH_2$—, —$CH_2CH_2$—, and —$CH_2(CH_2)_aCH_2$— in which the quantity, a, is 1 or 2 are preferred. The structures, —$CH_2$— and —$CH_2CH_2CH_2$— are most preferred.

Representative examples of $G^2$ include those listed for $G^1$ and also include —$CH_2$(—$CH$)$CH_2$—, and any of the isomers of —$CH_2CH$-(cyclohexyl)-, —$CH_2CH$-(cyclohexanol)-, and —$CH_2CH$-(norbornenyl)-.

The preferred embodiments of the present invention include mixtures of silicon-containing chemical compounds of Formula (I) in which: the sulfur silane condensates are derived from any of the bis-(3-triethoxysilyl-1-propyl) thioether or polysulfides wherein the quantity, x, of Formulae (II) and (III) is 1 to 8, any of the bis-(triethoxysilylmethyl) thioether or polysulfides wherein the quantity, x, of Formulae (II) and (III) is 1 to 8, or any of the bis-(triethoxysilylethyl) thioether or polysulfide isomers wherein the quantity, x, of Formulae (II) and (III) is 1 to 8 by loss of one or more ethoxy groups, and in which the alkylalkoxy silane condensates are derived from tetraethoxysilane, tetramethoxysilane, methyltriethoxysilane, ethyltriethoxysilane, propyltriethoxysilane, phenyltriethoxysilane, octyltriethoxysilane, and/or octadecyltriethoxysilane by loss of one or more ethoxy groups.

There are two key components for any method to prepare any of the chemical compositions of the present invention. The first is the use of alkoxysilane starting materials and the presence of water to effect partial hydrolysis of silane alkoxy groups and subsequent or concurrent coupling of the silane groups via Si—O—Si linkages. These Si—O—Si linkages derive their silicon atoms from the original alkoxysilanes and the O atoms from the water used in the process. The conversion of the starting alkoxysilane bonds to Si—O—Si can be brought to completion, but is preferably brought to only partial completion by limiting the quantity of water introduced into the process. Partial completion insures that alkoxy groups will remain on silicon in the final composition, which facilitate eventual coupling to the fillers used with the present compositions in their intended application. The water used in the preparation of the compositions of the present invention can be water per se, water in the form of a hydrated chemical species or salt (e.g., hydrated sodium sulfide), or water which has been used to couple silicon atoms to form Si—O—Si bonds via a previous process. Thus, in the last process, water could, for example, be added in the form of a siloxane or silicone oil. In such a process, the silicone oil would, itself, have been derived by reacting a silane containing hydrolyzable groups such as, but not limited to alkoxysilanes with water.

The second key component for any preparation of the chemical compositions of the present invention is the use of a sulfur anion to displace a leaving group from a carbon atom, by a chemical reaction, herein referred to as a sulfur anion displacement reaction. The sulfur anion displacement reaction, typically but not necessarily a nucleophilic displacement reaction, is shown below in Equations I and II for the preparation of the hybrid silanes whose structures are given by Formulae (II) and (III), respectively:

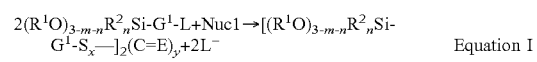

Equation I

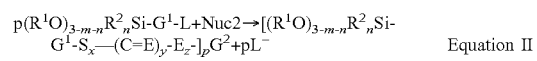

Equation II

Anions corresponding to L may be chloride, bromide, iodide, sulfate, and any of the sulfonates such as but not limited to tosylate, benzenesulfonate, and triflate, with chloride being preferable due to commercial availability. Bromide is preferable in cases where an enhanced reactivity relative to the chloride is desired, such as in aromatic halogen substitutions, which require driving conditions. Nuc1 and Nuc2 are sulfur anions which can be represented by the structures given by Formula (V) and Formula (VI), respectively, or, in the case of Formula (VI), their partially but not fully protonated derivatives.

$$\mathrm{Nuc1} = (^-S_x)_2(C=E)_y \qquad \text{(Formula V)}$$

$$\mathrm{Nuc2} = [^-S_x-(C=E)_y-E_z-]_p G^2 \qquad \text{(Formula VI)}$$

E, and the quantities, x, y, z, and p are defined as above.

Examples of Nuc1 and Nuc2 would include, but are not limited to sulfide, disulfide, trisulfide, tetrasulfide, pentasulfide, hexasulfide, heptasulfide, octasulfide, hydrosulfide, trithiocarbonate, and dithiocarbonate, and any of the thiocarboxylates and dithiocarboxylates. Other examples would include the polysulfide analogs of trithiocarbonate, dithiocarbonate, and any of the thiocarboxylates and dithiocarboxylates; i.e. structures of Formula (4) in which x and/or z is greater than 1.

Particularly useful sulfur anions include sulfide, polysulfide (which occur as mixtures of sulfide, disulfide, and trisulfide, tetrasulfide, etc.), hydrosulfide, trithiocarbonate trithiocarbonate analogs containing fewer than three sulfur atoms (hereafter referred to collectively as thiocarbonates), and so forth. Sodium sulfide is commercially available as a hydrate containing about 40% by weight of water. Hydrated sodium hydrosulfide, NaSH, is similarly available. It can also be generated by addition of hydrogen sulfide to solutions of sodium sulfide prepared from the readily available sodium sulfide described above. Hydrated sodium polysulfides are readily available and can also be readily prepared by the addition of elemental sulfur to solutions of hydrated sodium sulfide. The thiocarbonates can readily be prepared from hydrated sodium sulfide by addition of such readily available materials as carbon disulfide, carbonyl sulfide, and/or carbon dioxide. The thiocarbonates can be further converted to their respective polysulfidic analogs by addition of elemental sulfur. All of the aforementioned materials in anhydrous form, however, are difficult to prepare because of their great affinity for water and chemical reactivity. Hydrous NaSH loses hydrogen sulfide and forms sulfide salts with attempts to drive off the water thermally and/or with a vacuum. Anhydrous sodium sulfide oxidizes in air with sufficient ease, especially at the elevated temperatures required to drive off the water, so as to be pyrophoric. The polysulfide salts are more stable, and can be substantially dehydrated, but alkoxysilane derivatives prepared from them in otherwise anhydrous media always contain higher concentrations of Si—O—Si condensation products than do the derivatives prepared from polysulfide salts which were themselves prepared in anhydrous media, thereby demonstrating that some water always remains with any reasonable attempts to drive the water from hydrous polysulfide salts thermally. Since the thiocarbonates are prepared from sulfide salts, they would also only be readily available only as hydrates.

The present invention includes a particularly efficient method of using coupling agents for elastomers. Anhydrous salts of sulfur anions need not be used. In fact, the readily available hydrous salts are preferable for use in the preparation of the chemical compositions of the present invention due to the presence of Si—O—Si bonds in their structure which are derived from the water present in the hydrous salts of the sulfur anions used to prepare them. The inclusion of water distinguishes over other methods that exclude water. By incorporating water with the help of the alkylalkoxysilanes into the very structure of the coupling agent, two advantages are realized: 1) the chemical compositions of the present invention enhance processability and/or properties of rubber compositions over rubber compositions prepared using the analogous sulfur silanes prepared in anhydrous media, and 2) the chemical compositions of the present invention can be prepared from readily available hydrous raw materials eliminating the need for costly and hazardous methods required to generate the anhydrous analogs.

Practical methods for the preparation of the compositions of the present invention depend on how water is introduced, how much is introduced, when it is introduced, and on the order in which the alkylalkoxysilanes and the sulfur silanes and/or sulfur silane precursors are added. Certain combinations of the above would bring about an apparent exclusion of the alkylalkoxysilanes, $F^2$, from the Si—O—Si bonding, thus producing mixtures of alkylalkoxysilanes and Si—O—Si derivatives of sulfur silanes, instead of the desired hybrid silanes. Similarly, other combinations of the above would bring about an apparent exclusion of the sulfur silanes from the Si—O—Si bonding, thus producing mixtures of sulfur silanes and Si—O—Si derivatives of alkylalkoxysilanes, instead of the desired hybrid silanes. Both of these scenarios, however, are resolved by a final scrambling of Si—O—Si/alkoxy bonding at a point during or after the completion of both the initial alkoxysilane hydrolysis and sulfur anion displacement reactions. Such scrambling occurs readily under the reaction conditions, especially in the presence of acidic or basic substances, and also in the presence of ions and salts. The final product is therefore, with all three methods, not a mixture in which either the alkylalkoxysilane or the sulfur silane remains totally in the form of an alkoxysilane without involvement in Si—O—Si bonding, but rather, a true hybrid silane.

Hydrous sulfur anions may be dehydrated with one or more alkylalkoxysilanes prior to the sulfur anion displacement reaction. Using this method, a solution of the desired sulfur anion is first prepared. Hydrous sodium sulfide is dissolved in the alcohol corresponding to the alkoxy groups present on silicon, or other suitable solvent such as lower boiling point alcohols including methanol. Additional reagents are then added as appropriate to convert the sulfide anion into the desired anion. Using this method, an excess of hydrogen sulfide is used in order to convert the sulfide anion to the hydrosulfide anion from which would generate mercapto functionality in the hybrid silane. Elemental sulfur converts the sulfide anion to a distribution of sulfide and polysulfide anions which would generate thioether, disulfide, and/or polysulfide functionality in the hybrid silane, the distribution being dependent on how much sulfur was added. Carbon disulfide converts the sulfide anion to the trithiocarbonate anion which would generate trithiocarbonate functionality in the hybrid silane. Carbonyl sulfide and/or carbon dioxide generates anions and hybrid silane functionality analogous to those generated with carbon disulfide, but with one or two of the sulfur atoms replaced by oxygen, thus yielding hybrid silane functionalities such as thiocarbonate, dithiocarbonate, and thiothionocarbonate. Alternatively, a hydrous alkali metal salt of the desired anion could be dissolved in the alcohol directly.

Regardless of the method chosen to generate the hydrous alcoholic solution of the desired sulfur anion, the second step of this method involves adding the desired alkylalkoxy silane, either neat or as an alcoholic solution, to the hydrous alcoholic solution of the desired sulfur anion. A chemical reaction subsequently occurs in which the water present in the solution hydrolyzes the silicon alkoxy groups and brings about Si—O—Si coupling. If an excess of the alkylalkoxysilane is added in this step, all of the water is consumed and a distribution of alkylalkoxysiloxanes is generated. With an excess of water, all of the alkoxy groups are converted to Si—O—Si groups and/or Si—OH groups, and the remaining water will then further hydrolyze the alkoxy groups of the silanes yet to be added. Thus, adding an excess of water results in a hybrid of this method.

With the water partially or completely removed from the sulfur anion solution, the third step of this method is to add the chloroalkylsilane corresponding to the sulfur silane desired, whereupon two types of chemical reactions occur more or less simultaneously: First, the chloride ion leaving group is displaced by the sulfur anion to form the desired sulfur silane with concomitant co-product salt precipitation, and second, the alkoxy groups of the starting chloroalkyl silane and of the generated sulfur silane exchange with the Si—O—Si groups generated from the alkylalkoxy silane in the second step of this method. Although chloroalkyl silanes are the most commonly available, the starting silane could also be functionalized with any other suitable leaving group instead of chlorine. The aforementioned chloroalkyl silanes or their analogs containing leaving groups other than chloride will hereafter be referred to as sulfur silane precursors. Upon completion of the reaction, the salt precipitate produced is filtered off, the solvent is removed by evaporation, and any salt that had been dissolved in the solvent is then filtered off, leaving the behind the desired hybrid silane.

A second method of preparing the compositions of the present invention involves simultaneous Si—O—Si coupling and sulfur anion displacement reactions. Using this method, a solution of the sulfur anion is prepared as described above. However, using this method, both the sulfur silane precursor and the alkylalkoxy silane are added together to the sulfur anion solution, rather than sequentially, allowing the water to directly couple both types of silanes via Si—O—Si linkages. Scrambling of the Si—O—Si linkages, once formed, can occur as described above, but the complete Si—O—Si structure of the hybrid silane is formed immediately rather than in a later step.

A third method of preparing the silane-sulfur hybrids of the present invention also involves concurrent sulfur silane Si—O—Si coupling and sulfur anion displacement reactions, but subsequently followed by Si—O—Si scrambling with alkylalkoxy silanes. Using this method, the sulfur anion solution is prepared as described for the two methods above. The second step is the addition of the sulfur silane precursor. As described in the first method above, only one of the two types of alkoxysilanes is initially added to the sulfur anion solution, and as a result, the initial Si—O—Si framework generated from the water present in this solution excludes the other alkoxysilane type. Also as described in the first method above, an excess of water relative to the alkoxysilane present can bring about complete hydrolysis and Si—O—Si coupling of the Si alkoxy groups with water left over to couple the other alkoxysilane type so as to effect a hybridization of this method with Method 2. The difference is that in Method 3, the sulfur silane precursor is initially present to take up the water, instead of the alkylalkoxy silane. The third step is then the addition of the alkylalkoxy silane prior to filtration, solvent removal, and final filtration, during which time Si—O—Si scrambling occurs to generate the hybrid silane. A novel feature of Method 3 is that the alkylalkoxysilane can be added after addition of the sulfur silane precursor, but before it has completely reacted, in which the final Si—O—Si framework is generated by a combination of direct formation and scrambling of pre-formed Si—O—Si bonds.

A fourth method of preparing the sulfur-silane hybrid of the present invention involves what may be referred to as sulfur silane-alkylalkoxy silane (Si—O—Si) scrambling. This method is an adaptation of the first three methods described above in which the sulfur silane or its partially or completely hydrolyzed derivative is initially prepared either from anhydrous or hydrous reagents, respectively, and optionally isolated. It is then used as a partial or complete replacement for the sulfur silane precursors in the second step of the methods previously described above. If used as a complete replacement, the need to perform the first step in the process is eliminated.

The four methods described above are discrete ways of categorizing the procedure based mainly on the order of addition of the reagents, and on what happens chemically as a result of these actions. In practice, any sequence that involves the addition of the sulfur silane precursor and the alkylalkoxy silane to the non-anhydrous sulfur anion solution will ultimately bring about formation of the hybrid silane. The arrangement of the Si—O—Si network to form the hybrid silane occurs most expeditiously if an acid or base catalyst is present, and is also aided by the presence of the salt co-product, either precipitated or in solution. The sulfur anion used as the reagent also makes a good catalyst.

Alcohols are typically the preferred solvents because they readily dissolve the sulfur anions, mediate the chemical reactions readily, and lead to coarse precipitates which are readily filtered. Other solvents, however, can be used as well, such as ethers, tetrahydrofuran, polyethers, glyme, diglyme and higher glymes, aromatic solvents such as toluene and xylene providing that the sulfur anion is sufficiently soluble, dimethylformamide, dimethylsulfoxide, N-methylpyrrolidinone, and so forth. The latter solvent is preferred for substitutions directly on aromatic rings.

If alcohol solvents are used, the preparation of the hybrid silanes can also be coupled with a transesterification of the alkoxy group by using or substituting the solvent with another alcohol at any step prior to solvent removal. The distillation of the alcohol from the mixture can be accompanied by an exchange of the alkoxy group on silicon in which it is replaced by the alkoxy group corresponding to the alcohol solvent introduced. Thus, less volatile alcohols readily displace alkoxy groups corresponding to the more volatile alcohol groups. The reverse can also be accomplished, but requires at least two coupled distillations. An example would be the use of methoxy sulfur silane precursors with alkylmethoxy silanes in ethanol, removing the solvent by fractional distillation and generating an ethoxy hybrid silane.

The hybrid silanes of the present invention are unique in that they combine the coupling characteristics of the sulfur silanes with the dispersion characteristic of the alkylalkoxysilanes in a single molecule. The hybrid silanes described herein are useful as coupling agents for organic polymers (i.e., rubbers) and inorganic fillers. Unlike the use of mixtures of these types of silanes, in which a given site on silica contains either a coupling silane or a dispersing silane, the hybrid silanes provide both characteristics at every site, thereby allowing for better incorporation of the filler into the polymer matrix at the molecular level. It is this feature along with the high molecular weights of the hybrid silanes which contribute to the very low volatilities, and gives the hybrid silanes certain advantages such as the ability to bring about lower processing viscosity, better desirable filler dispersion, less premature curing (scorch), and reduced odor.

Elastomers useful with the coupling agents described herein include sulfur vulcanizable rubbers including conjugated diene homopolymers and copolymers, and copolymers of at least one conjugated diene and aromatic vinyl compound. Suitable organic polymers for preparation of rubber compositions are well known in the art and are described in various textbooks including *The Vanderbilt Rubber Handbook*, Ohm, R.F., R.T. Vanderbilt Company, Inc. (1990) and in the *Manual for the Rubber Industry*, Kemperman, T. and Koch Jr., S., Bayer A G, LeverKusen (1993).

One example of a suitable polymer for use herein is solution-prepared styrene-butadiene rubber (SSBR). This solution prepared SBR typically has a bound styrene content in a range of about 5 to about 50 wt. %, preferably about 9 to about 36 wt. %. Other useful polymers include styrene-butadiene rubber (SBR), natural rubber (NR), ethylene-propylene copolymers and terpolymers (EP, EPDM), acrylonitrile-butadiene rubber (NBR), polybutadiene (BR), and so forth. The rubber composition is comprised of at least one diene-based elastomer, or rubber. Suitable conjugated dienes are isoprene and 1,3-butadiene and suitable vinyl aromatic compounds are styrene and alpha methyl styrene. Polybutadiene may be characterized as existing primarily, typically about 90 wt. %, in the cis-1,4-butadiene form.

Preferably, the polymer is a sulfur curable rubber. Such diene based elastomer, or rubber, may be selected, for example, from at least one of cis-1,4-polyisoprene rubber (natural and/or synthetic, preferably natural), and preferably natural rubber, emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (about 35 to about 50 wt. % vinyl), high vinyl polybutadiene rubber (about 50 to about 75 wt. % vinyl), styrene/isoprene copolymers, emulsion polymerization prepared styrene/butadiene/acrylonitrile terpolymer rubber and butadiene/acrylonitrile copolymer rubber.

For some applications, an emulsion polymerization derived styrene/butadiene (E-SBR) having a relatively conventional styrene content of about 20 to about 28 wt. % bound styrene, or an E-SBR having a medium to relatively high bound styrene content of about 30 to about 45 wt. % may be used.

Emulsion polymerization prepared styrene/butadiene/acrylonitrile terpolymer rubbers containing about 2 to about 40 wt. % bound acrylonitrile in the terpolymer are also contemplated as diene based rubbers for use in this invention.

A particulate filler may also be added to the crosslinkable elastomer compositions of the present invention including siliceous fillers, carbon black, and so forth. The filler materials useful herein include, but are not limited to, carbon black and metal oxides such as silica (pyrogenic and precipitated), titanium dioxide, aluminosilicate and alumina, clays and talc, and so forth.

Particulate, precipitated silica is also sometimes used for such purpose, particularly when the silica is used in conjunction with a silane. In some cases, a combination of silica and carbon black is utilized for reinforcing fillers for various rubber products, including treads for tires. Alumina can be used either alone or in combination with silica. The term, alumina, can be described herein as aluminum oxide, or $Al_2O_3$. The fillers may be hydrated or in anhydrous form.

The hybrid silane composition(s) may be premixed or pre-reacted with the filler particles, or added to the rubber mix during the rubber and filler processing, or mixing stages. If the hybrid silane composition(s) and filler are added separately to the rubber mix during the rubber and filler mixing, or processing stage, it is considered that the hybrid silane composition(s) then combine(s) in an in-situ fashion with the filler.

The vulcanized rubber composition should contain a sufficient amount of filler to contribute a reasonably high modulus and high resistance to tear. The combined weight of the filler may be as low as about 5 to about 100 parts per hundred rubber (phr), but is more preferably from about 25 to about 85 phr.

Preferably, at least one precipitated silica is utilized as a filler. The silica may be characterized by having a BET surface area, as measured using nitrogen gas, preferably in the range of about 40 to about 600 $m^2/g$, and more usually in a range of about 50 to about 300 $m^2/g$. The BET method of measuring surface area is described in the *Journal of the American Chemical Society*, Volume 60, pg. 304 (1930). The silica typically may also be characterized by having a dibutylphthalate (DBP) absorption value in a range of about 100 to about 350, and more usually about 150 to about 300. Further, the silica, as well as the aforesaid alumina and aluminosilicate, may be expected to have a CTAB surface area in a range of about 100 to about 220. The CTAB surface area is the external surface area as evaluated by cetyl trimethylammonium bromide with a pH of 9. The method is described in ASTM D 3849.

Mercury porosity surface area is the specific surface area determined by mercury porosimetry. Using this method, mercury is penetrated into the pores of the sample after a thermal treatment to remove volatiles. Set up conditions may be suitably described as using a 100 mg sample; removing volatiles during 2 hours at 105° C. and ambient atmospheric pressure; ambient to 2000 bars pressure measuring range. Such evaluation may be performed according to the method described in Winslow, Shapiro in ASTM bulletin, pg. 39 (1959) or according to DIN 66133. For such an evaluation, a CARLO-ERBA Porosimeter 2000 might be used. The average mercury porosity specific surface area for the silica should be in a range of about 100 to about 300 $m^2/g$.

A suitable pore size distribution for the silica, alumina and aluminosilicate according to such mercury porosity evaluation is considered herein to be such that about 5% or less of its pores have a diameter of less than about 10 nm, about 60 to 90% of its pores have a diameter of about 10 to about 100 nm, about 10 to 30% of its pores have a diameter at about 100 to about 1,000 nm, and about 5 to 20% of its pores have a diameter of greater than about 1,000 nm.

The silica might be expected to have an average ultimate particle size, for example, in the range of about 10 to about 50 nm as determined electron microscopy, although the silica particles may be even smaller, or possibly larger, in size. Various commercially available silicas may be considered for use in this invention such as, from PPG Industries under the HI-SIL™ trademark with designations HI-SIL™ 210, 243, etc.; silicas available from Rhone-Poulenc, with, for example, designation of ZEOSIL™ 1165MP; silicas available from Degussa-Huels with, for example, designations VN2 and VN3, etc., and silicas commercially available from Huber having, for example, a designation of HUBER-SIL™ 8745.

In compositions for which it is desirable to utilize siliceous fillers such as silica, alumina and/or aluminosilicates in combination with carbon black reinforcing pigments, the compositions may comprise a filler mix of about 15 to about 98 wt. % of the siliceous filler, and about 2 to about 85 wt. % carbon black, wherein the carbon black has a CTAB value in a range of about 80 to about 150. Alternately, a portion of the carbon black may be a grade with extremely high surface area, up to about 800 m²/g. The weight ratio may range from about 3/1 to about 30/1 for siliceous fillers to carbon black. More typically, it is desirable to use a weight ratio of siliceous fillers to carbon black of at least about 3/1, and preferably at least about 10/1.

Alternatively, the filler can be comprised of about 60 to about 95 wt. % of said silica, alumina and/or aluminosilicate and, correspondingly, about 40 to about 5 wt. % carbon black. The siliceous filler and carbon black may be pre-blended or blended together in the manufacture of the vulcanized rubber.

In preparing the rubber compositions of the present invention, one or more of the hybrid silane compositions are mixed with the organic polymer before, during or after the compounding of the filler into the organic polymer. It is preferred to add the hybrid silane composition(s) before or during the compounding of the filler into the organic polymer, because these silanes facilitate and improve the dispersion of the filler. The total amount of hybrid polysulfide silane composition present in the resulting combination should be about 0.05 to about 25 phr, more preferably about 1 to about 10 phr. Fillers can be used in quantities ranging from about 5 to about 100 phr, more preferably from about 25 to 80 phr.

In practice, sulfur vulcanized rubber products typically are prepared by thermomechanically mixing rubber and various ingredients in a sequentially step-wise manner followed by shaping and curing the compounded rubber to form a vulcanized product. First, for the aforesaid mixing of the rubber and various ingredients, typically exclusive of sulfur and sulfur vulcanization accelerators (collectively, curing agents), the rubber(s) and various rubber compounding ingredients typically are blended in at least one, and often (in the case of silica filled low rolling resistance tires) two, preparatory thermomechanical mixing stage(s) in suitable mixers. Such preparatory mixing is referred to as nonproductive mixing or non-productive mixing steps or stages. Such preparatory mixing usually is conducted at temperatures of about 140° C. to about 200° C., and for some compositions, about 150° C. to about 180° C.

Subsequent to such preparatory mix stages, in a final mixing stage, sometimes referred to as a productive mix stage, curing agents, and possibly one or more additional ingredients, are mixed with the rubber compound or composition, at lower temperatures of typically about 50° C. to 130° C. in order to prevent or retard premature curing of the sulfur curable rubber, sometimes referred to as scorching. The rubber mixture, also referred to as a rubber compound or composition, typically is allowed to cool, sometimes after or during a process intermediate mill mixing, between the aforesaid various mixing steps, for example, to a temperature of about 50° C. or lower. When it is desired to mold and to cure the rubber, the rubber is placed into the appropriate mold at a temperature of at least about 130° C. and up to about 200° C. which will cause the vulcanization of the rubber by the sulfur-containing groups on the hybrid silane composition(s) and any other free sulfur sources in the rubber mixture.

Thermomechanical mixing refers to the phenomena whereby under the high shear conditions in a rubber mixer, the shear forces and associated friction occurring as a result of mixing the rubber compound, or some blend of the rubber compound itself and rubber compounding ingredients in the high shear mixer, the temperature autogeneously increases, i.e. it "heats up". Several chemical reactions may occur at various steps in the mixing and curing processes.

The first reaction is a relatively fast reaction and is considered herein to take place between the filler and the silane alkoxide group of the hybrid silane composition(s). Such reaction may occur at a relatively low temperature such as, for example, at about 120° C. The second reaction is considered herein to be the reaction which takes place between the sulfur-containing portion of the hybrid silane composition(s), and the sulfur vulcanizable rubber at a higher temperature, for example, above about 140° C.

Another sulfur source may be used, for example, in the form of elemental sulfur, such as but not limited to $S_8$. A sulfur donor is considered herein as a sulfur containing compound which liberates free, or elemental sulfur, at a temperature in a range of about 140° C. to about 190° C. Such sulfur donors may be, for example, although are not limited to, polysulfide vulcanization accelerators and organosilane polysulfides with at least two connecting sulfur atoms in its polysulfide bridge. The amount of free sulfur source addition to the mixture can be controlled or manipulated as a matter of choice relatively independently from the addition of the aforesaid hybrid silane composition(s). Thus, for example, the independent addition of a sulfur source may be manipulated by the amount of addition thereof and by the sequence of addition relative to the addition of other ingredients to the rubber mixture.

A desirable rubber composition may therefore comprise about 100 parts by weight of at least one sulfur vulcanizable rubber selected from the group consisting of conjugated diene homopolymers and copolymers, and copolymers of at least one conjugated diene and aromatic vinyl compound, about 5 to about 100 phr, preferably about 25 to 80 phr of at least one particulate filler, up to about 5 phr of a curing agent, and about 0.05 to about 25 phr of at least one hybrid silane composition as described in the present invention.

The filler preferably comprises from about 1 to about 85 wt. % carbon black based on the total weight of the filler, and about 0 to about 20 wt. % of at least one hybrid silane composition(s) based on the total weight of the filler.

The rubber composition may then be prepared by first blending polymer, filler and hybrid silane composition(s), or polymer, filler pretreated with all or a portion of the hybrid silane composition(s) and any remaining hybrid silane composition(s), in a first thermomechanical mixing step to a temperature of about 140° C. to about 200° C. for about 2 to about 20 minutes, preferably about 4 to about 15 minutes. Additional thermomechanical mixing steps may be performed with intermittent cooling. The cooling may be performed by removal of the rubber from the mixer. Optionally, the curing agent is then added in another thermomechanical mixing step at a temperature of about 50° C. and mixed for about 1 to about 30 minutes. The temperature is then heated again to between about 130° C. and about 200° C. and curing is accomplished in about 5 to about 60 minutes.

The process may also comprise the additional steps of preparing an assembly of a tire or sulfur vulcanizable rubber with a tread comprised of the rubber composition prepared according to this invention and vulcanizing the assembly at a temperature in a range of about 130° C. to about 200° C.

Other optional ingredients may be added in the rubber compositions of the present invention including curing aids, i.e., sulfur compounds, including activators, retarders and accelerators, processing additives such as oils, plasticizers, tackifying resins, silicas, other fillers, pigments, fatty acids, zinc oxide, waxes, antioxidants and antiozonants, peptizing agents, reinforcing materials such as, for example, carbon black, and so forth. Such additives are selected based upon the intended use and on the sulfur vulcanizable material selected for use, and such selection is within the knowledge of one of skill in the art, as are the required amounts of such additives known to one of skill in the art.

The vulcanization may be conducted in the presence of additional sulfur vulcanizing agents. Examples of suitable sulfur vulcanizing agents include, for example elemental sulfur (free sulfur) or sulfur donating vulcanizing agents, for example, an amino disulfide, polymeric polysulfide or sulfur olefin adducts which are conventionally added in the final, productive, rubber composition mixing step. The sulfur vulcanizing agents are used, or added in the productive mixing stage, in an amount ranging from about 0.4 to about 3 phr, or even, in some circumstances, up to about 8 phr, with a range of from about 1.5 to about 2.5 phr, sometimes from about 2 to about 2.5 phr being preferred.

Optionally, vulcanization accelerators, i.e., additional sulfur donors, may be used herein. It is appreciated that they may be, for example, of the type such as, for example, benzothiazole, alkyl thiuram disulfide, guanidine derivatives and thiocarbamates. Representative of such accelerators are, for example, but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-betahydroxy ethyl piperazine) and dithiobis(dibenzyl amine). Other additional sulfur donors, may be, for example, thiuram and morpholine derivatives. Representative of such donors are, for example, but not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally and preferably, a primary accelerator(s) is used in total amounts ranging from about 0.5 to about 4 phr, preferably about 0.8 to about 1.5 phr. Combinations of a primary and a secondary accelerator might be used with the secondary accelerator being used in smaller amounts, about 0.05 to about 3 phr, in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

Amounts of tackifier resins, if used, may comprise about 0.5 to about 10 phr, usually about 1 to about 5 phr. Processing aids may comprise about 1 to about 50 phr. Such processing aids can include, for example, aromatic, napthenic, and/or paraffinic processing oils. Anti-oxidants may comprise about 1 to about 5 phr. Representative anti-oxidants may be, for example, diphenyl-p-phenylenediamine and others, for example, those disclosed in the *Vanderbilt Rubber Handbook*, pgs. 344–346 (1978). Amounts of anti-ozonants may comprise about 1 to about 5 phr. Fatty acids, if used, which can include stearic acid, comprise about 0.5 to about 3 phr. Zinc oxide may comprise about 2 to about 5 phr. Amounts of waxes may comprise about 1 to about 5 phr. Often microcrystalline waxes are used. Peptizers may comprise about 0.1 to about 1 phr and may be, for example, pentachlorothiophenol and dibenzamidodiphenyl disulfide.

The rubber composition of this invention can be used for various purposes. For example, it can be used for various tire compounds. Such tires can be built, shaped, molded and cured by various methods which are known and will be readily apparent to those having skill in such art.

The examples presented below demonstrate significant advantages with the use of the hybrid silane compositions described herein relative to the use of simple polysulfide silanes of the currently practiced art, in their performance as coupling agents in silica-filled rubber. Table 1, listed in Examples 3 and 4, below, presents the performance parameters of hybrid silane compositions of the present invention and of TESPT, the silane used in the prior art which has become the industry standard. Scorch times for Silanes 1 and 2 are typically noticeably improved relative to the control. The 300% modulus of Silane 1 at both loadings and of Silane 2 at the lower loading is substantially improved in each case, over the control: 14.8, 14.1, and 15.3 megapascals, respectively, versus 12.6 megapascals for the control. Silane 1 imparted a noticeable reduction in the value of Tan Delta at 60° C. relative to the control (0.085 vs. 0.103), which is an indicator for someone skilled in the art for improved rolling resistance in tire tread applications. In addition to these performance advantages, Silanes 1 and 2 were prepared in one step, directly from hydrous sodium sulfide, whereas the control must be prepared under the more hazardous and costly anhydrous conditions currently practiced in the art.

All references cited herein are incorporated by reference herein in their entirety. The following nonlimiting examples are further illustrative of the present invention, but are in no way intended to be construed as limiting the invention in any way.

EXAMPLES

Example 1 (Silane 1)

Preparation of a Tetraethoxysilane-bis-(3-triethoxysilyl-1-propyl)polysulfide Hybrid Silane Composition Hydrous sodium sulfide (40% $H_2O$; 60% $Na_2S$; 65 g, 0.50 moles) supplied in flake form from Fisher Scientific, and 500 g of absolute ethanol were introduced into a 3-liter flask equipped with a reflux condenser. The mixture was maintained under an atmosphere of nitrogen using a nitrogen bubbler. Control of the vacuum was enhanced via a bleeder valve inserted between the cold trap and the distillation head. The flask was heated using an electric heating mantle regulated by a variable voltage controller. The voltage controller was coupled to an electronic temperature regulator responsive to the height of mercury in a mercury thermometer which was inserted directly into the mixture in 3-liter flask. The mixture was refluxed with stirring until the flakes had dissolved to give a light yellow-brown, nearly clear solution. Stirring was accomplished using a Teflon® coated stirring bar to prevent adherence of any solution to the bar.

The heating was discontinued and the solution allowed to cool to 40° C., whereupon powdered sulfur (41.6 g, 1.30 moles) was added with continued stirring. The sulfur dissolved within several minutes, accompanied by a modest increase in temperature, to form a deep reddish-brown solution. Tetraethoxysilane (624.9 g, 3.0 moles) was then added to the solution with continued stirring and the solution was brought to reflux and maintained for several hours. Heating was discontinued and 3-chloro-1-propyltriethoxysilane (240 g, 1.00 moles) was slowly added to the still warm, stirred solution. Within a few minutes, the solution turned cloudy, and a precipitate of sodium chloride began to form. The rate of addition was adjusted so that the resulting exotherm maintained a smooth reflux. The reflux subsided shortly after the addition of the 3-chloro-1-propyltriethoxysilane was complete, whereupon power was supplied to the heating mantle to maintain a smooth reflux for an additional 3 hours. At this point, the reaction and sodium chloride formation was complete and heating was discontinued. The solution was allowed to cool to room temperature with continued stirring, and then decanted in a tall, narrow vessel. The clear liquid was poured off and the remaining slurry was shaken with fresh ethanol to extract more of the soluble product and the decantation and pouring off was repeated twice. The resulting three portions of clear liquid were combined. The precipitated sodium chloride in this fashion removed from the ethanolic solution of the hybrid silane. The ethanol was then removed by rotary evaporation to less than 1 torr at 65° C. This resulted in a turbid, brown liquid consisting of the hybrid silane and some additional sodium chloride which was dissolved in the ethanol and had thus escaped prior filtration. The hybrid silane was again filtered to remove the sodium chloride, resulting in the final product, which was a clear, brown liquid.

GCMS (gas chromatography coupled to mass spectrometry) indicated the presence of tetraethoxysilane (44.4%), bis(3-triethoxysilyl-1-propyl)disulfide together with smaller amounts of the trisulfide and thioether analogs, tetraethoxysilane condensates, polysulfide silane condensates, and hybrid silanes corresponding to cross condensates of tetraethoxysilane and the polysulfide silanes. The tetraethoxysilane condensates included hexaethoxydisiloxane (20.6%), octaethoxytrisiloxane (6.5%), together with peaks consistent with smaller quantities of decaethoxytetrasiloxane, tris-(triethoxysilyl)ethoxysilane, triethoxysilyl-heptaethoxy-cyclotrisiloxane, octaethoxycyclotetrasiloxane, and traces of higher homologs. The polysulfide silane condensates included the cyclosiloxane condensation products of bis(3-triethoxysilyl-1-propyl)disulfide and bis(3-triethoxysilyl-1-propyl)trisulfide. In addition, there were numerous peaks in the GC spectrum consistent with the siloxane cross-condensation products of bis(3-triethoxysilyl-1-propyl) polysulfides and tetraethoxysilane, corresponding to the hybrid silanes of the present invention. A partial list of these hybrid silane products included 3-triethoxysiloxy-3-diethoxysilyl-1-propyl-3'-triethoxysilyl-1'-propyl disulfide, bis(3-triethoxysiloxy-3-diethoxysilyl-1-propyl)disulfide, bis-(3-triethoxysiloxy)-3-ethoxysilyl-1-propyl-3'-triethoxysilyl-1'-propyl disulfide, bis(3-(3-triethoxysilyl-1-propyldithio)-1-propyldiethoxysiloxy)diethoxysilane, isomers of bis(3-(3-triethoxysilyl-1-propyldithio)-1-propyldiethoxysiloxy)tetraethoxycyclotrisiloxane, isomers of 3-(3-triethoxysilyl-1-propyldithio)-1-propyldiethoxysiloxypentaethoxycyclotrisiloxane, and analogous trisulfide species. Percentages were determined as peak area percent values.

SFC (supercritical fluid chromatography) analysis using a carbon dioxide mobile phase confirmed the presence of many of the species noted in the paragraph above, along with additional polysulfide species including bis(3-triethoxysilyl-1-propyl)tetrasulfide, bis(3-triethoxysilyl-1-propyl)pentasulfide, bis(3-triethoxysilyl-1-propyl)hexasulfide, bis(3-triethoxysilyl-1-propyl)heptasulfide, and bis(3-triethoxysilyl-1-propyl)octasulfide; and most combinations of their bis-disiloxane condensation products. The presence of the aforementioned hybrid silanes was also confirmed, along with many of their higher-sulfur-rank (i.e., tetrasulfide, pentasulfide, etc.) analogs. The higher-sulfur-rank species were only found in the SFC because these species are unstable at the high temperatures (up to 250° C.) used in the GC injection port and column.

Example 2 (Silane 2)

Preparation of a Dimethyldiethoxysilane-bis-(3-triethoxysilyl-1-propyl)polysulfide Hybrid Silane Composition The same procedure was used as in Example 1. Hydrous sodium sulfide (60%; 65 g, 0.50 moles) and 500 g of absolute ethanol were introduced into the 3-liter flask and refluxed with stirring until the flakes had dissolved to give a light yellow-brown, nearly clear solution. The heating was discontinued and this solution was allowed to cool to 40° C., whereupon powdered sulfur (41.6 g, 1.30 moles) was added with continued stirring. The sulfur dissolved within several minutes, accompanied by a modest increase in temperature, to form a deep reddish-brown solution. Dimethyldiethoxysilane (889 g, 6.00 moles) was then added to the solution with continued stirring. The solution was brought to and maintained at reflux for several hours. Heating was discontinued and 3-chloro-1-propyltriethoxysilane (240 g, 1.00 moles) was slowly added to the still warm, stirred solution. Within a few minutes, the solution turned cloudy, and a precipitate of sodium chloride began to form. The rate of addition was adjusted so that the resulting exotherm maintained a smooth reflux. The reflux subsided shortly after the addition of the 3-chloro-1-propyltriethoxysilane was complete, whereupon power was supplied to the heating mantle to maintain a smooth reflux for an additional 3 hours. At this point, the reaction and sodium chloride formation was complete and heating was discontinued. The solution was allowed to cool to room temperature with continued stirring, and then decanted in a tall, narrow vessel. The clear liquid was poured off and the remaining slurry was shaken with fresh ethanol to extract more of the soluble product and the decantation and pouring off was repeated twice. The resulting three portions of clear liquid were combined. These decantings removed the precipitated sodium chloride from the ethanolic solution of the hybrid silane. The ethanol was then removed by rotary evaporation to less than 1 torr at 65° C. This resulted in a turbid, brown liquid consisting of the hybrid silane and some additional sodium chloride which had escaped the prior filtration because it had been dissolved in the ethanol. The hybrid silane was again filtered to remove the sodium chloride, resulting in the final product, which was a clear, brown liquid.

GCMS analysis indicated the presence of dimethyldiethoxysilane (1.3%), bis(3-triethoxysilyl-1-propyl)disulfide together with smaller amounts of the trisulfide and thioether analogs, dimethyldiethoxysilane condensates, polysulfide silane condensates, and hybrid silanes corresponding to cross condensates of dimethyldiethoxysilane and the polysulfide silanes. The dimethyldiethoxysilane condensates included 1,1,3,3-tetramethyl-1,3-diethoxydisiloxane (16.9%), 1,1,3,3,5,5-hexamethyl-1,3,5-triethoxytrisiloxane (14.3%), 1,1,3,3,5,5,7,7-octamethyl-1,3,5,7-tetraethoxytetrasiloxane (6.0%), and 1,1,3,3,5,5,7,7,9,9-decamethyl-1,3,5,7,9-pentaethoxypentasiloxane (3.9%), together with smaller quantities of several higher homologs. The polysulfide silane condensates included the cyclosiloxane condensation products of bis(3-triethoxysilyl-1-propyl)disulfide and bis(3-triethoxysilyl-1-propyl)trisulfide. In addition, there were numerous peaks in the GC spectrum consistent with the siloxane cross-condensation products of bis(3-triethoxysilyl-1-propyl) polysulfides and dimethyldiethoxysilane, corresponding to the hybrid silanes of the present invention. A partial list of these hybrid silane products included 3-ethoxydimethylsiloxy-3-diethoxysilyl-1-propyl-3'-triethoxysilyl-1'-propyl disulfide, bis(3-ethoxydimethylsiloxy-3-diethoxysilyl-1-propyl)disulfide, bis-(3-ethoxydimethylsiloxy)-3-ethoxysilyl-1-propyl-3'-triethoxysilyl-1'-propyl disulfide, bis(3-(3-triethoxysilyl-1-propyldithio)-1-propyldiethoxysiloxy)dimethylsilane, isomers of bis(3-(3-triethoxysilyl-1-propyldithio)-1-propyldiethoxysiloxy)tetramethylcyclotrisiloxane, isomers of 3-(3-triethoxysilyl-1-propyldithio)-1-propyldiethoxysiloxyethoxytetramethylcyclotrisiloxane, and analogous trisulfide species. Percentages were determined as peak area percent values.

SFC analysis using a carbon dioxide mobile phase confirmed the presence of many of the species noted in the paragraph above, along with additional polysulfide species including bis(3-triethoxysilyl-1-propyl)tetrasulfide, bis(3-triethoxysilyl-1-propyl)pentasulfide, bis(3-triethoxysilyl-1-propyl)hexasulfide, bis(3-triethoxysilyl-1-propyl)heptasulfide, and bis(3-triethoxysilyl-1-propyl)octasulfide; and most combinations of their bis-disiloxane condensation products. The presence of the aforementioned hybrid silanes was also confirmed, along with many of their higher-sulfur-rank (i.e. tetrasulfide, pentasulfide, etc.) analogs. The higher-sulfur-rank species were only found in the SFC because these species are unstable at the high temperatures (up to 250°) used in the GC injection port and column.

Examples 3 and 4

The hybrid silane compositions prepared in Examples 1 and 2 were used as the coupling agents to prepare low rolling resistance tire tread formulations. The rubber composition used was the following, where the figures listed under the PHR heading indicate the mass of the corresponding ingredient used relative to 100 total mass units of polymer (in this case, SSBR and polybutadiene) used:

| PHR | Ingredient |
|---|---|
| 75 | SSBR (12% styrene, 46% vinyl, $T_g$: 42° C.) |
| 25 | cis-1,4-polybutadiene (98% cis, $T_g$: 104° C.) |
| 80 | Silica (150–190 $m^2$/gm, ZEOSIL ® 1165MP, Rhone-Poulenc) |
| 32.5.1.1 | Aromatic process oil (high viscosity, Sundex ™ 8125, Sun Oil Co., Inc. (Sunoco)) |
| 2.5 | Zinc oxide (KADOX ™ 720C, Zinc Corp) |
| 1 | Stearic acid (INDUSTRENE ™, Crompton Corp.) |
| 2 | 6PPD antiozonant (SANTOFLEX ™ 6PPD, Flexsys Corp.) |
| 1.5 | Microcrystalline wax (M-4067, Schumann Inc.) |
| 3 | N330 carbon black (Engineered Carbons, Inc.) |
| 1.4 | Sulfur (#104, Sunbelt Co.) |
| 1.7 | CBS accelerator (SANTOCURE ™, Flexsys Corp.) |
| 2 | DPG accelerator (PERKACIT ™ DPG-C, Flexsys Corp.) |

The hybrid silane compositions prepared by the procedures described in Examples 1 and 2 were used to prepare the rubber compositions described in Examples 3 and 4, respectively. A control was run side by side with Examples 3 and 4 to provide a meaningful basis of comparison for the performance as a coupling agent in silica-filled rubber of the representative examples presented herein of the hybrid silane compositions. The silane used in the control was the current industry standard coupling agent for rubber for silica-filled tire treads, the nominal bis(3-triethoxysilyl-1-propyl)tetrasulfide (TESPT). The rubber compounding formulations and procedures used in Examples 3 and 4 and in the control were identical with exceptions only in the hybrid silane composition used as the coupling agent and in the loading levels of the hybrid silane composition used and the elemental sulfur used in the curatives. Two rubber formulations were prepared and evaluated in each of Example 3 and Example 4, corresponding to the two sets of columns in Table 1 under the headings, Example 3 and Example 4. The first of each of the two sets of columns describes a rubber formulation in which the loading of hybrid silane composition was chosen so as to deliver a constant loading of sulfur silane silicon, relative to the control. This means that only the silicon from the sulfur silane portion of the hybrid silane composition, only the $F^1$ portion of Formula (I), was considered and that the silicon from the alkylalkoxy silane portion of the hybrid silane composition, the $F^2$ portion of Formula (I), was disregarded. The rationale for this was that the sulfur silane portion of the coupling agent is the one which actually couples polymer to filler. The second of each of the two sets of columns describes the other extreme, which is a rubber formulation in which the loading of hybrid silane composition was chosen so as to deliver a constant loading of total silicon from the hybrid silane composition, relative to the control. This means that both the silicon from the sulfur silane portion of the hybrid silane composition, the $F^1$ portion of Formula (I), and the silicon from the alkylalkoxy silane portion of the hybrid silane composition, the $F^2$ portion of Formula (I), were considered. The rationale for this was that all of the silicon of the coupling agent has the potential to become involved in polymer to filler coupling in that all of the silicon is expected to couple at least to the filler, and thereby, indirectly also to the polymer by virtue of the Si—O—Si bonds within the hybrid silanes, which link the alkylalkoxy portion of the coupling agent to the sulfur silane portion. The loadings of elemental sulfur in the curatives were adjusted so as to maintain a constant level, relative to the control, of total sulfur delivered to the formulation. Thus, actual loadings of coupling agent and elemental sulfur varied due to what amounts to equivalent weight differences among the coupling agents evaluated.

The samples were prepared using a "Model B BANBURY"™ (Farrell Corp.) mixer with a 103 $in^3$ (1690 cc) chamber volume. A rubber masterbatch was prepared in a two step procedure. The mixer was set at 120 rpm with the cooling water on full. The rubber polymers were added to the mixer while running and ram down mixed for 30 seconds. Approximately half of the silica (about 35 to 40 g), and all of the hybrid silane composition (in an ethylvinyl acetate (EVA) bag) were added and ram down mixed for 30 seconds. The remaining silica and the oil (in an EVA bag) were then added and ram down mixed for 30 seconds. The mixer throat was dusted down three times and the mixture ram down mixed for 15 seconds each time. The mixing speed was increased to between about 160 to about 240 rpm as required to raise the temperature of the rubber masterbatch to between about 160 and about 165° C. in approximately 1 minute. The masterbatch was removed from the mixer and using this composition, a sheet was then formed on a roll mill set at about 50 to about 60° C., and then allowed to cool to ambient temperature.

The masterbatch was then again added to the mixer with the mixer at 120 rpm and cooling water turned on full and ram down mixed for 30 seconds. The remainder of the ingredients were then added and ram down mixed for 30 seconds. The mixer throat was dusted down, and the mixer speed was increased to about 160 to about 240 rpm in order to increase the temperature of the mix to about 160 to about 165° C. in approximately 2 minutes. The rubber composition was mixed for 8 minutes with adjustments to the mixer speed in order to maintain the temperature between about 160 to about 165° C. The composition was removed from the mixer and a sheet about inch thick was formed on a 6×12 inch roll mill set at about 50 to about 60° C. This sheet was then allowed to cool to ambient temperature.

The resulting rubber composition was subsequently mixed with the curatives on a 6 in.×13 in. (15 cm×33 cm) two roll mill that was heated to between 50 and 60° C. The sulfur and accelerators were then added to the composition and thoroughly mixed on the roll mill and allowed to form a sheet. The sheet was cooled to ambient conditions for about 24 hours before it was cured.

The rheological properties of the rubber compound so prepared were measured on a Monsanto R-100 Oscillating Disk Rheometer and a Monsanto M1400 Mooney Viscometer. A Rheometrics ARES was used for dynamic mechanical analysis. The specimens for measuring the mechanical properties were cut from 6 mm plaques cured for 35 minutes at 160° C. or from 2 mm plaques cured for 25 minutes at 160° C. The hybrid silane compositions, whose preparations were described in Examples 1 and 2, were compounded into the tire tread formulation according to the above procedure. In Example 3, the hybrid silane composition prepared in Example 1 was used, and in Example 4, the hybrid silane composition prepared in Example 2 was used.

These examples were tested against a control sample which is nominally bis-(3-triethoxysilyl-1-propyl)tetrasulfide (TESPT), an industry standard coupling agent. Its actual composition is a mixture of polysulfides, with significant contributions from individual species containing chains of from 2 to 8 sulfur atoms. The compositions were tested using standard testing procedures. The results of the testing are summarized in Table 1 below.

TEST METHODS

1. Mooney Scorch
   ASTM D1646.
2. Mooney Viscosity
   ASTM D1646.
3. Oscillating Disc Rheometer (ODR)
   ASTM D2084.
4. Physical Properties; Storage Modulus Loss Modulus, Tensile & Elongation
   ASTM D412 and D224.
5. DIN Abrasion
   DIN Procedure 53516.
6. Heat Buildup
   ASTM D623.
   Heat build-up was measured at 100° C. using an 18.5% compression, 143 psi load and a 25 minute run. A sample which was at ambient conditions was placed in an oven that had been preheated to 100° C. The sample was conditioned at 100° C. for 20 minutes and then given a 5 minute test run.
7. % Permanent Set
   ASTM D623.
8. Shore A Hardness
   ASTM D2240.

TABLE 1

Properties and Processing Parameters of Rubber Compounded in Examples 3 and 4 Using the Coupling Agents Prepared in Examples 1 and 2, Respectively

| Silane: Type and Amount | Example 3 Silane 1 | | Example 4 Silane 2 | | Control TESPT |
|---|---|---|---|---|---|
| Silane Loading (phr) | 18.3 | 7.0 | 10.0 | 7.0 | 7.0 |
| Elemental Sulfur in Curatives (phr) | 1.4 | 2.35 | 1.4 | 1.86 | 1.4 |
| Mooney Viscosity @ 100° C. (ML1 + 4) | 81 | 69 | 93 | 71 | 73 |
| Mooney Scorch @ 135° C., minutes | | | | | |
| MS1 + $t_3$ | 6.6 | 7.7 | 6.6 | 8.0 | 6.3 |
| MS1 + $t_{18}$ | 8.3 | 9.7 | 7.5 | 9.3 | 8.6 |
| MS1 + | 51.7 | 35.1 | 57.4 | 40.8 | 43.2 |
| ODR @ 149° C., 1° Arc; 30 minutes | | | | | |
| $M_L$, dN-m | 10.5 | 9.2 | 10.7 | 9.3 | 9.0 |
| $M_L$, lb-in | 9.3 | 8.1 | 9.5 | 8.2 | 8.0 |
| $M_H$, dN-m | 37.6 | 36.4 | 37.6 | 38.3 | 31.1 |
| $M_H$, lb-in | 33.3 | 32.2 | 33.3 | 33.9 | 27.5 |
| $t_{s1}$, minutes | 4.1 | 4.8 | 3.9 | 4.9 | 4.1 |
| $t_{90}$, minutes | 15.4 | 17.6 | 13.6 | 16.3 | 18.0 |
| Physical Properties; 90 minute cure @ 149° C. | | | | | |
| Shore A Hardness | 61 | 62 | 62 | 63 | 58 |
| % Elongation | 357 | 416 | 430 | 382 | 406 |
| 25% Modulus, Mpa | | | | | |
| 25% Modulus, psi | | | | | |
| 100% Modulus, Mpa | 2.52 | 2.35 | 2.19 | 2.63 | 1.91 |
| 100% Modulus, psi | 365 | 341 | 318 | 381 | 277 |
| 200% Modulus, Mpa | 7.50 | 6.87 | 6.36 | 7.85 | 5.72 |
| 200% Modulus, psi | 1088 | 996 | 922 | 1138 | 829 |
| 300% Modulus, Mpa | 14.83 | 14.09 | 12.89 | 15.26 | 12.62 |

TABLE 1-continued

Properties and Processing Parameters of Rubber Compounded in Examples 3
and 4 Using the Coupling Agents Prepared in Examples 1 and 2, Respectively

| Silane: Type and Amount | Example 3 Silane 1 | | Example 4 Silane 2 | | Control TESPT |
|---|---|---|---|---|---|
| 300% Modulus, psi | 2150 | 2043 | 1869 | 2212 | 1830 |
| 400% Modulus, Mpa | | 21.25 | 19.54 | | 20.05 |
| 400% Modulus, psi | | 3081 | 2833 | | 2907 |
| Tensile Strength, Mpa | 18.98 | 22.24 | 21.48 | 21.55 | 20.49 |
| Tensile Strength, psi | 2752 | 3225 | 3115 | 3125 | 2971 |
| Reinforcement Index (300%/25% Mod.) | | | | | |
| Reinforcement Index (300%/100% Mod.) | 5.88 | 6.00 | 5.89 | 5.80 | 6.61 |
| Dynamic Mechanical Analysis @ 0.15% Strain, torsion mode (2nd sweep) | | | | | |
| $G' \times 10^{-7}$, dyn/cm$^2$; @ 0° C., 1 Hz | 6.8083 | | 7.4502 | | 4.5625 |
| 10 Hz | 8.4568 | | 9.3692 | | 5.7529 |
| $G' \times 10^{-7}$, dyn/cm$^2$; @ 60° C, 1 Hz | 3.4851 | | 3.3269 | | 2.2990 |
| 10 Hz | 3.8918 | | 3.8142 | | 2.6401 |
| $G'' \times 10^{-7}$, dyn/cm$^2$; @ 0° C., 1 Hz | 0.9933 | | 1.1598 | | 0.7111 |
| 10 Hz | 1.6753 | | 1.9041 | | 1.2383 |
| $G'' \times 10^{-7}$, dyn/cm$^2$; @ 60° C., 1 Hz | 0.2645 | | 0.3036 | | 0.2050 |
| 10 Hz | 0.3315 | | 0.3961 | | 0.2720 |
| Tan Delta @ 0° C., 1 Hz | 0.1459 | | 0.1557 | | 0.1559 |
| 10 Hz | 0.1981 | | 0.2032 | | 0.2153 |
| Tan Delta @ 60° C., 1 Hz | 0.0759 | | 0.0913 | | 0.0892 |
| 10 Hz | 0.0852 | | 0.1039 | | 0.1030 |
| Ratio of Tan Delta (0° C./60° C.), 1 Hz | 1.922 | | 1.705 | | 1.748 |
| 10 Hz | 2.325 | | 1.956 | | 2.090 |
| Dynamic Mechanical Analysis @ 3% Strain, torsion mode (2nd sweep) | | | | | |
| $G' \times 10^{-7}$, dyn/cm$^2$; @ 0° C., 1 Hz | 4.2296 | | 4.3388 | | |
| 10 Hz | 5.1007 | | 5.1404 | | |
| $G' \times 10^{-7}$, dyn/cm$^2$; @ 60° C., 1 Hz | 2.7121 | | 2.7545 | | |
| 10 Hz | 2.9899 | | 3.0569 | | |
| $G'' \times 10^{-7}$, dyn/cm$^2$; @ 0° C., 1 Hz | 0.9985 | | 1.0953 | | |
| 10 Hz | 1.6027 | | 1.6157 | | |
| $G'' \times 10^{-7}$, dyn/cm$^2$; @ 60° C., 1 Hz | 0.2900 | | 0.3502 | | |
| 10 Hz | 0.3696 | | 0.4559 | | |
| Tan Delta @ 0° C., 1 Hz | 0.2361 | | 0.2524 | | |
| 10 Hz | 0.3142 | | 0.3143 | | |
| Tan Delta @ 60° C., 1 Hz | 0.1069 | | 0.1271 | | |
| 10 Hz | 0.1236 | | 0.1491 | | |
| Ratio of Tan Delta (0° C./60° C.), 1 Hz | 2.209 | | 1.986 | | |
| 10 Hz | 2.542 | | 2.108 | | |
| Heat Build-up, 100° C., 17.5% Compression, 990 Kpa (143 psi) static load, 25 minute run | | | | | |
| Delta T, ° C. | 29 | 25 | 22 | 22 | 23 |
| % Permanent Set | 10.3 | 9.9 | 6.2 | 6.2 | 6.2 |

Unit Conversions:
1 Mpa (megapascal) = $10^6$ N/m$^2$ = $10^7$ dyn/cm$^2$ = 145.0377 psi
1 psi = 68947.6 dyn/cm$^2$
1 lb-in = 1.13 dN-m The present invention offers an alternative route to analogs of the aforementioned coupling agents whereby hydrated sodium sulfide, polysulfide, and hydrosulfide salts can be used as raw materials. The molecular structure of the coupling agents is altered at the silicon atom but not at the sulfur atom relative to that of the coupling agents derived from prior art anhydrous sodium sulfide, polysulfide, and hydrosulfide salts. This altered molecular structure can furthermore be used to advantage by proper adjustment of the manufacturing process to yield coupling agents which perform better than the analogs prepared by current conventional methods.

What is claimed is:

1. A process of making a hybrid silane composition comprising the steps of hydrolyzing a sulfur silane and a nonsulfur silane in the presence of a hydrated alkali metal salt to effect partial hydrolysis of silane alkoxy groups on each of the sulfur silane and nonsulfur silane, and bonding the partially hydrolyzed sulfur silane and nonsulfur silane to each other via Si—O—Si linkages, said hybrid silane composition comprising a mixture of compounds corresponding to the general formula:

$F^1_r F^2_s$  Formula (I)

wherein
r is 0 to 10,000;
s is 0 to 10,000;
with the proviso that r and s each have a value of at least 1 for at least one compound of Formula (I) in the mixture of compounds;
$F^1$ is a sulfur silane structure selected from the group consisting of:

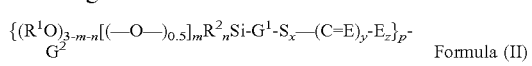
$\{(R^1O)_{3-m-n}[(-O-)_{0.5}]_m R^2_n Si-G^1-S_x-(C=E)_y-E_z\}_p-G^2$  Formula (II)

and

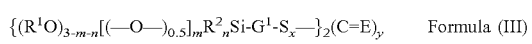
$\{(R^1O)_{3-m-n}[(-O-)_{0.5}]_m R^2_n Si-G^1-S_x-\}_2(C=E)_y$  Formula (III)

wherein each occurrence of $R^1$ and $R^2$ is independently hydrogen, or any group which can be obtained by removal of one hydrogen atom from a hydrocarbon group having from 1 to 20 carbon atoms, including branched or straight chain alkyl, alkenyl, aryl or aralkyl groups;

each occurrence of $G^1$ is any group which can be obtained by removal of a quantity of two hydrogen atoms from any hydrocarbon having from 1 to 20 carbon atoms;

each occurrence of $G^2$ is independently a hydrogen atom or any group which can be obtained by removal of a quantity of p hydrogen atoms from any hydrocarbon having from 1 to 20 carbon atoms;

S is sulfur;

O is oxygen;

Si is silicon;

each occurrence of E is independently oxygen or $S_x$;

each occurrence of m and n is independently 0, 1 or 2;

each occurrence of p is independently 1 to 4;

each occurrence of y is 1 and z is independently 0 or 1; and each occurrence of x is independently 1 to 8;

$F^2$ is a nonsulfur silane structure represented by the general formula:

    Formula (IV)

wherein each occurrence of $R^1$ is as defined above;

each occurrence of $R^3$ is independently hydrogen, or a hydrocarbon group of 1 to 20 carbon atoms including aryl as well as branched or straight chain alkyl, alkenyl, arenyl, or aralkyl groups; and each occurrence of m' and n' can be independently 0, 1, 2 or 3.

2. The process of claim 1 wherein the hydrated alkali metal salt is selected from the group consisting of hydrated alkali metal sulfide, polysulfide, hydrosulfide salt and mixtures thereof.

3. The process of claim 1 wherein the sulfur silane is selected from the group consisting of bis-(3-triethoxysilyl-1-propyl)dithiocarbonate and bis-(3-triethoxysilyl-1-propyl) trithiocarbonate.

4. The process of claim 1 wherein the nonsulfur silane is selected from the group consisting of tetraethoxysilane, tetramethoxysilane, triethoxysilane, tetraisopropoxysilane, tetrapropoxysilane, methyltriethoxysilane, methyltrimethoxysilane, ethyltriethoxysilane, propyltriethoxysilane, propyltrimethoxysilane, phenyltriethoxysilane, phenyltrimethoxysilane, octyltriethoxysilane, octyltrimethoxysilane, octadecyltriethoxysilane, and octadecyltrimethoxysilane.

5. A process of making a hybrid silane composition comprising the steps of hydrolyzing a sulfur silane and a nonsulfur silane in the presence of water to effect partial hydrolysis of silane alkoxy groups on each of the sulfur silane and nonsulfur silane, and bonding the partially hydrolyzed sulfur silane and nonsulfur silane to each other via Si—O—Si linkages, said hybrid silane composition comprising a mixture of compounds corresponding to the general formula:

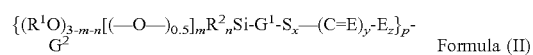    Formula (I)

wherein r is 0 to 10,000;

s is 0 to 10,000;

with the proviso that r has a value of at least 1 for at least one compound of Formula (I) in the mixture of compounds;

$F^1$ is a sulfur silane structure selected from the group consisting of:

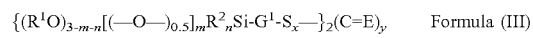    Formula (II)

and

    Formula (III)

wherein each occurrence of $R^1$ and $R^2$ is independently hydrogen, or any group which can be obtained by removal of one hydrogen atom from a hydrocarbon group having from 1 to 20 carbon atoms, including branched or straight chain alkyl, alkenyl, aryl or aralkyl groups;

each occurrence of $G^1$ is any group which can be obtained by removal of a quantity of two hydrogen atoms from any hydrocarbon having from 1 to 20 carbon atoms;

each occurrence of $G^2$ is independently a hydrogen atom or any group which can be obtained by removal of a quantity of p hydrogen atoms from any hydrocarbon having from 1 to 20 carbon atoms;

S is sulfur;

O is oxygen;

Si is silicon;

each occurrence of E is independently oxygen or $S_x$;

each occurrence of m and n is independently 0, 1 or 2;

each occurrence of p is independently 1 to 4;

each occurrence of y and z is independently 0 or 1; and each occurrence of x is independently 1 to 8;

$F^2$ is a nonsulfur silane structure represented by the general formula:

$(R^1O)_{4-m'-n'}[(-O-)_{0.5}]_{m'}R^3{}_{n'}Si$    Formula (IV)

wherein each occurrence of $R^1$ is as defined above;

each occurrence of $R^3$ is independently hydrogen, or a hydrocarbon group of 1 to 20 carbon atoms including aryl as well as branched or straight chain alkyl, alkenyl, arenyl, or aralkyl groups; and each occurrence of m' and n' can be independently 0, 1, 2 or 3, wherein the source of water is an alkali metal salt.

6. The process of claim 5 wherein the alkali metal salt is an alkali metal salt selected from the group consisting of hydrated alkali metal sulfide, polysulfide, hydrosulfide salt and mixtures thereof.

* * * * *